United States Patent
Wallace

(10) Patent No.: US 6,655,197 B2
(45) Date of Patent: Dec. 2, 2003

(54) AUTOMATIC TRANSMISSION FLUID CHARACTERISTIC MONITORING SYSTEM EMPLOYED FOR REPAIR/MAINTENANCE AND DURING OPERATION OF A LAND MOTOR VEHICLE

(75) Inventor: Ben Wallace, Saxtons River, VT (US)

(73) Assignee: Sonnax Industries, Inc., Bellows Falls, VT (US)

( * ) Notice: Subject to any disclaimer, the term of this patent is extended or adjusted under 35 U.S.C. 154(b) by 278 days.

(21) Appl. No.: 09/910,350

(22) Filed: Jul. 23, 2001

(65) Prior Publication Data
US 2003/0015027 A1 Jan. 23, 2003

(51) Int. Cl.$^7$ .............................................. G01M 19/00
(52) U.S. Cl. ...................................... 73/118.1
(58) Field of Search ................................ 73/116, 118.1, 73/117.2, 117.3; 74/501.3 R, 733.1, 731.1, 501 R; 340/449

(56) References Cited

U.S. PATENT DOCUMENTS

| | | |
|---|---|---|
| 1,585,976 A | 5/1926 | Groves et al. |
| 1,607,716 A | 11/1926 | Adams |
| 2,303,532 A | 12/1942 | Ewart et al. |
| 3,196,673 A | 7/1965 | Carson |
| 4,250,744 A | 2/1981 | Vinokurov et al. |
| 4,656,880 A | 4/1987 | Hildebrand et al. |
| 4,682,493 A | 7/1987 | Tenenbaum |
| 5,107,246 A | 4/1992 | Mogaki |
| 5,309,790 A | 5/1994 | Tanaka |
| 5,319,963 A | 6/1994 | Benford |
| 5,638,721 A | 6/1997 | Lee |
| 5,700,226 A | 12/1997 | Droste |
| 5,808,187 A | 9/1998 | Gooden et al. |
| 6,038,918 A | 3/2000 | Newton |

Primary Examiner—Edward Lefkowitz
Assistant Examiner—Maurice Stevens
(74) Attorney, Agent, or Firm—Stephen E. Feldman

(57) ABSTRACT

The present invention is directed towards an apparatus for monitoring and displaying characteristic values of certain parameters of the automatic transmission fluid in the automatic transmission system or the automatic transaxle system of a land motor vehicle. The apparatus has several elements to it: a sensor, which is placed into a conduit carrying the automatic transmission fluid to read the characteristic values, microprocessor, which receives these values, and finally a readout component, which displays them. The characteristic values of the automatic transmission fluid may include the values for the flow rate, pressure, temperature, and others. The readout component may be a diagnostic tool used for maintenance and/or repair or a dashboard display component used by the driver or the operator of the motor vehicle while the vehicle is in motion.

13 Claims, 4 Drawing Sheets

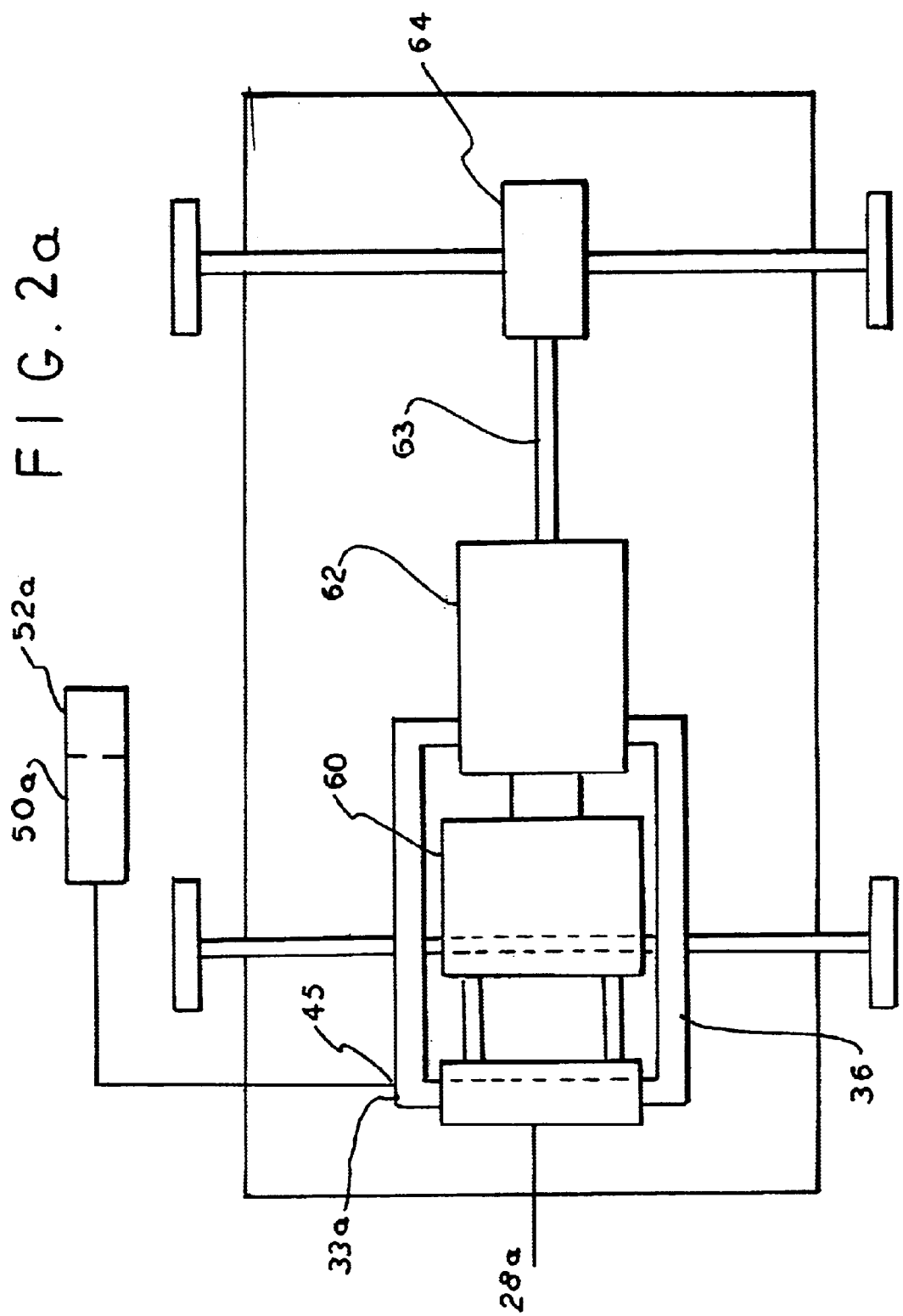

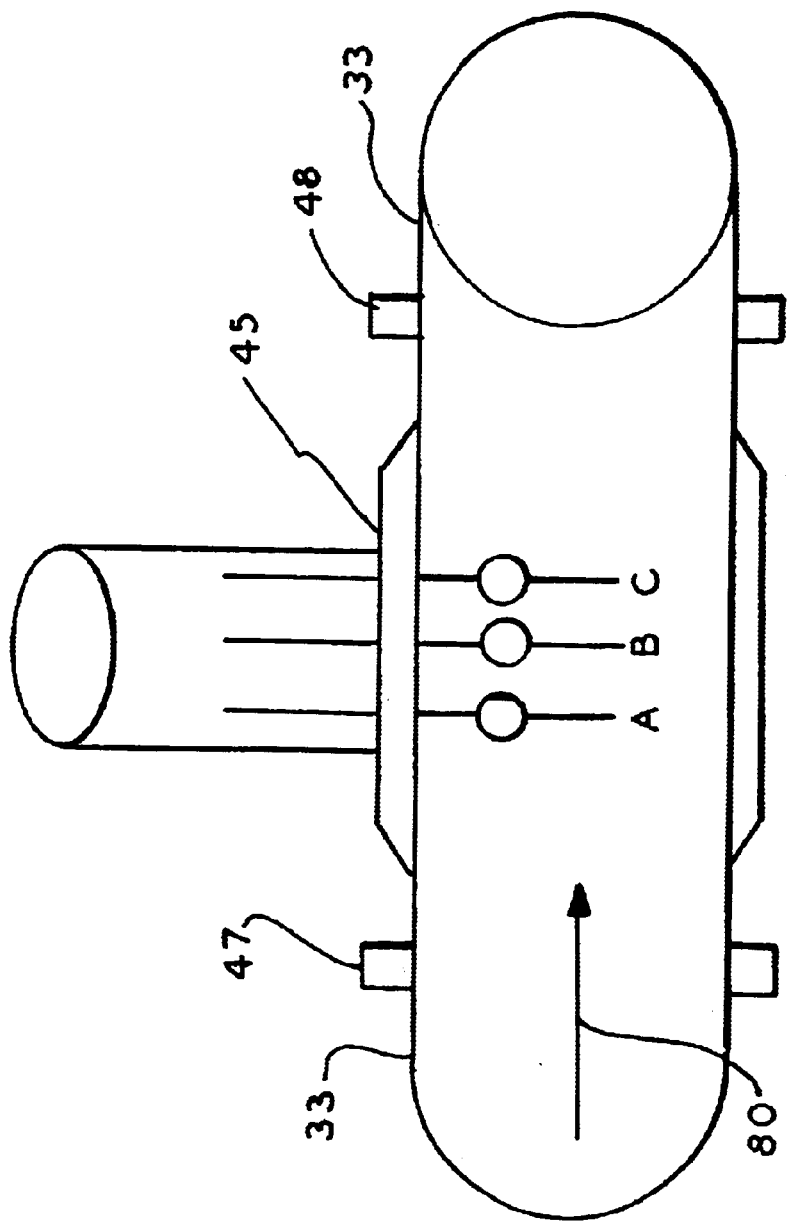

AUTOMATIC TRANSMISSION FLUID CHARACTERISTIC MONITORING SYSTEM EMPLOYED FOR REPAIR/MAINTENANCE AND DURING OPERATION OF A LAND MOTOR VEHICLE

FIELD OF THE INVENTION

The present invention relates to an apparatus and a system for monitoring automatic transmission fluid in an automatic transmission system of a land motor vehicle and in an automatic transaxle system of a land motor vehicle. The apparatus and system are used for the purposes of maintenance and/or repair and serve as a diagnostic tool to the operator or the driver of the motor vehicle while the vehicle is in operating condition.

BACKGROUND OF THE INVENTION

Contemporary land motor vehicles have at least three systems or a system of components for their operation. These include:

1) a power plant, which may be an engine or a motor;
2) a transmission system, which may be a manual or an automatic shift system; and,
3) wheels, which conventionally are four in number.

An internal combustion engine is the most popular and commonly used component of a power plant in land motor vehicles. The internal combustion engine may be fueled by gasoline, diesel oil or natural gas or propane. Monitoring apparatus is coupled to the power plant and is, usually, located on the vehicle's dashboard, which provides an ongoing display of engine operation data for the operator or the driver of the motor vehicle, while the vehicle is in motion. The dashboard serves as an indicator for various engine data outputs and malfunction indications arising out of engine operation, if any. The engine operation data may be used to diagnose the health or condition of the power plant, during its operation. Other, more sophisticated monitoring apparatus, which may be coupled to the power plant on a temporary basis, may be used for a more detailed diagnosis, maintenance and/or repair of the power plant.

The automatic transmission system and the automatic transaxle system used on land motor vehicles are similar, in many respects. The automatic transmission system predates the automatic transaxle system. The most obvious difference between the two systems is that the automatic transmission system, while coupled to the power plant, includes final drive gears, a drive shaft and differential gears. The drive shaft remotely separates the final drive gears from the differential gears. The automatic transaxle system is, also, coupled to the power plant and includes the final drive gears and differential gears. All gears are intrinsic parts of the system. Automatic transmission systems are used on four-wheel drive and on rear-wheel drive land motor vehicles. Automatic transaxle systems are used on front-wheel drive land motor vehicles.

There are further similarities to the automatic transmission system and the automatic transaxle system. When the engine is in operating condition, both systems convert engine's torque into rotational power that drives the wheels of the vehicle. Both systems shift gears automatically according to the engine output power and speed. Both, also, use a hydraulic sub-system for changing gears and the hydraulic fluid of the hydraulic sub-system for lubricating contacting elements of the system. Although lubricated, there is a friction between the contacting elements in both systems and, because of that friction, the systems tend to heat up during operation. The systems use hydraulic fluid in the hydraulic sub-system to cool the systems. The hydraulic sub-system includes a cooling stage for cooling the hydraulic fluid. The cooling stage of the hydraulic sub-system includes a pump, for circulating the hydraulic fluid, and a cooling core or a radiator, through which the hydraulic fluid passes. The cooling core or the radiator serves to reduce the temperature of the hydraulic fluid. The hydraulic fluid, generally used in the hydraulic sub-system, is referred to as automatic transmission fluid (referred to as "ATF"). In a healthy automatic transmission system and a healthy automatic transaxle system, the operating temperature and operating circulation pressure of the ATF are maintained within predetermined values.

U.S. Pat. No. 5,700,226 to Droste teaches a system for providing an adequate volume of lubrication fluid to all mechanical components of an automatic transmission system and for producing that flow in a manner consistent with the operating requirements of the automatic transmission system. Inherent in the teaching of Droste is the vital importance of the condition of the ATF, the temperature of the ATF and circulating pressure of the ATF in the automatic transmission system. The Droste disclosure, however, does not mention the automatic transaxle system. The ATF, which is used in the hydraulic circuits and for lubrication of mechanical components in both the automatic transmission system and the automatic transaxle system, should be maintained at some predetermined level. Moreover, functionality of ATF requires certain operating temperatures, which have been determined by the manufacturer and/or designer of the system. In addition, for proper operation of the automatic transmission system, the ATF, in an operating transmission system, should be maintained within some predetermined pressure range, as determined by the manufacturer and/or designer of the transmission system.

For clarity and conciseness, hereinafter the terms automatic transmission and/or automatic transmission system shall include the automatic transmission system and the automatic transaxle system.

There are three major functions of the ATF in the automatic transmission system of a motor vehicle:

1) It serves as a hydraulic fluid for moving components of the automatic transmission system;
2) It serves as a lubricant for moving components of the automatic transmission system; and,
3) It serves as a coolant or heat transfer fluid for removing heat from the automatic transmission system, including its moving components and other parts of the automatic transmission system.

All of these functions place the ATF under a great strain. To accomplish this multi-use of the ATF, the hydraulic sub-system of an automatic transmission system includes:

1) Circulation of the ATF, via a hydraulic pump, through hydraulic circuit channels and the lubrication channels for lubrication;
2) Movement of components of the automatic transmission system to produce automatic shifting;
3) Cooling the components of the automatic transmission system and circulating the ATF through a heat transfer device to remove heat from the ATF.

Using ATF, as a lubricant and a coolant fluid, drives it to high temperatures, which are substantially higher than the recommended operating temperatures of the ATF. The ATF must be cooled. Cooling the ATF is accomplished by circulating it at some rate through a heat exchange unit, such as a radiator. To produce an adequate heat exchange, the circulation rate of ATF or the ATF's pressure in the system depend on the size and efficiency of the heat exchange unit and the heat coefficient of the ATF. This essentially requires a constant flow, at some predetermined rate, of the ATF through the automatic transmission system, including the cooling channels of the heat transfer elements of the radiator.

SUMMARY OF THE INVENTION

The object of the present invention is to provide a system for monitoring of automatic transmission fluid's characteristics in an automatic transmission (or transaxle) system of a land motor vehicle for maintenance and/or repair.

Another object of the present invention is to provide a system for monitoring of automatic transmission fluid's characteristics in an automatic transmission (or transaxle) system of a land motor vehicle for the operator or the driver of such motor vehicle, while the vehicle is in an operating condition.

The present invention provides an automatic transmission system hydraulic fluid characteristic monitoring system. Invention's components are conventionally well known to one skilled in the art and, thus, may be obtained. However, the unique combination of those components is not known. The invention provides a fluid sensor, mounted in a circulating channel of the ATF, located in the flow path of the ATF. The fluid sensor detects and monitors the presence of the ATF, the flow rate of the ATF in the circulation system and the pressure of the ATF, and, optionally, the temperature of the ATF. The data sensed by the fluid sensor from within the flow path of the ATF is applied to a microprocessor, which analyzes the data and outputs the information to a readout, connected to the microprocessor, displaying the data, preferably, in digital form. From the readout, an analysis of the health of the circulation sub-system and the ATF in the sub-system may be made. Moreover, the readout will serve as detection tool for problems affecting the automatic transmission system.

The present invention may be used as a maintenance and/or repair tool for the automatic transmission system. The invention is used for detection of blockages and/or restrictions created in the components of the circulation stage of the hydraulic sub-system, including the output of the pump component and functional irregularities in the moving components of the automatic transmission system, interfering with the ATF's circulation.

Moreover, the present invention provides an on-going monitoring system of the ATF flow in the automatic transmission of the motor vehicle. The invention, having a readout component, displays data on the dashboard of the motor vehicle. The data is displayed on the dashboard while the motor vehicle is in motion or being repaired. By viewing the readout data, the driver or the operator of the motor vehicle may analyze the status and the health of the automatic transmission system, while the motor vehicle is moving, and, thus, act accordingly, if there are any deviations from the normal operating conditions.

BRIEF DESCRIPTION OF THE DRAWINGS

FIG. 2a is a block diagram representing the invention used on a conventional rear-wheel drive motor vehicle; and FIG. 3 represents an in-line fluid sensor, for sensing characteristics in the ATF, used as a sensing element in the invention.

DESCRIPTION OF THE PREFERRED EMBODIMENT

Figure 1:
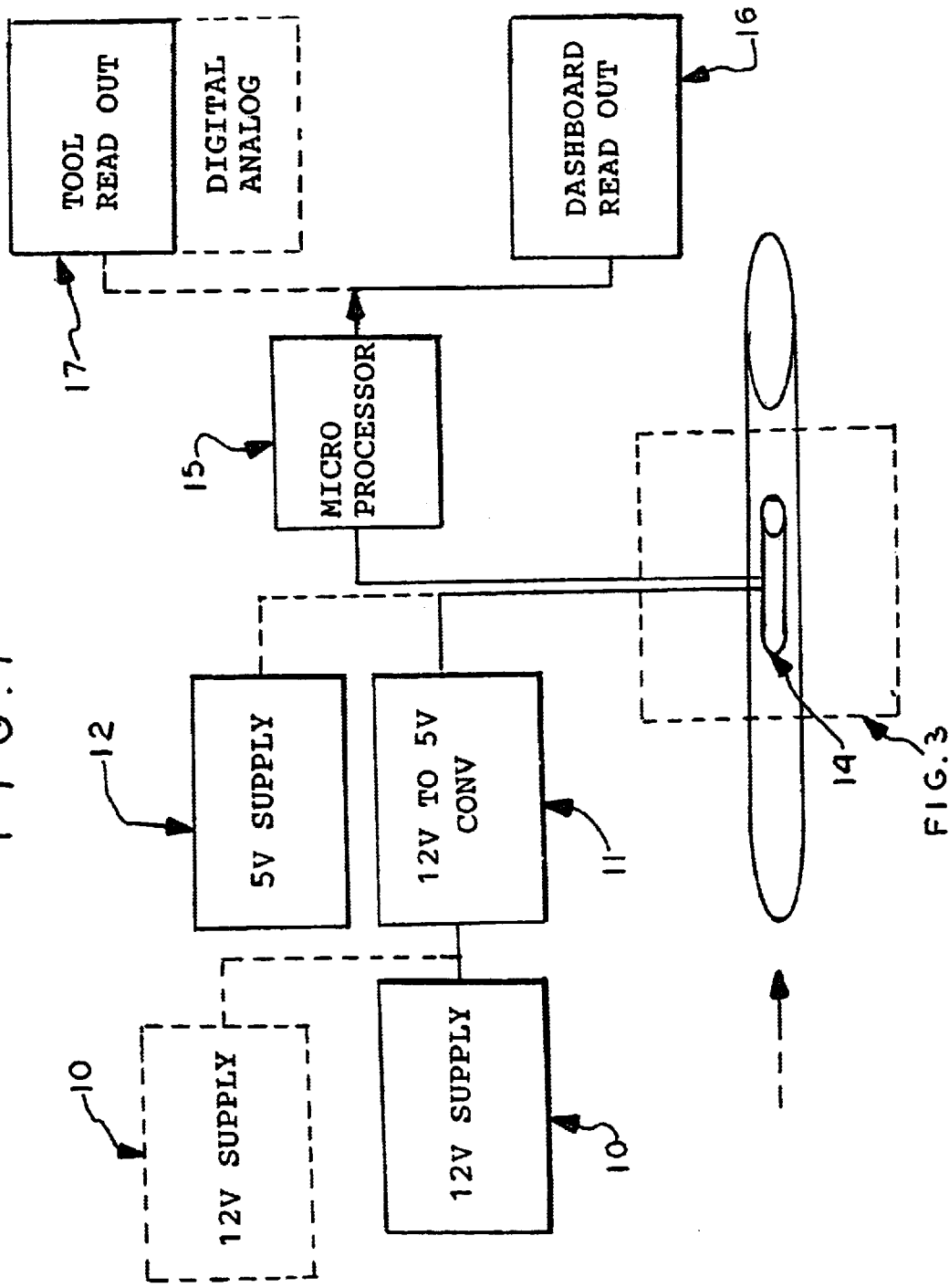
FIG. 1 is a block diagram representing the invention.
Figure 2:
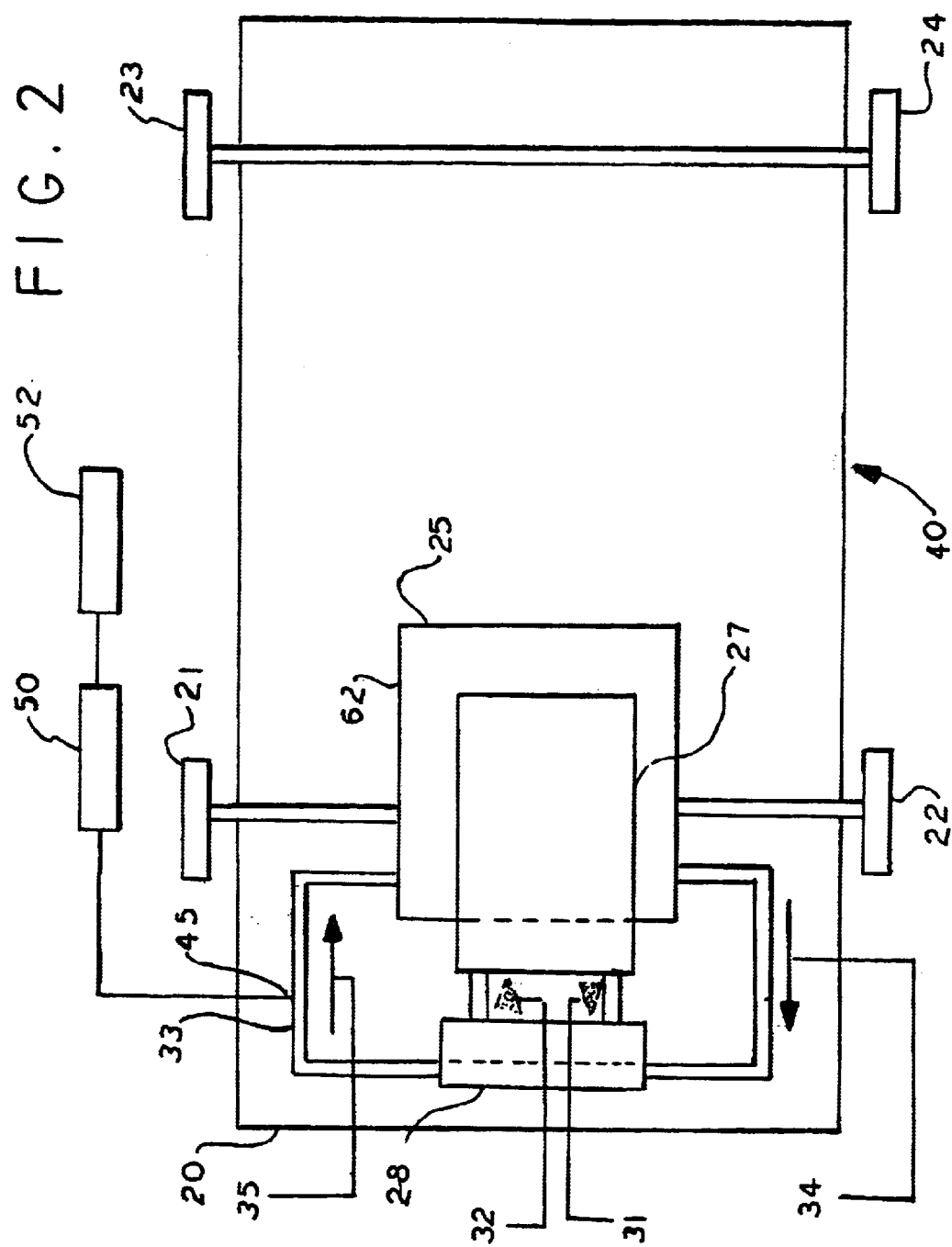
FIG. 2 is a block diagram representing the invention used on a conventional front-wheel drive land motor vehicle.

Referring to FIG. 1, the invention is presented with alternate arrangements. As represented in FIG. 1, the present transmission fluid monitoring system is electrically driven and, thus, may be connected to a 12-volt supply source. The vehicle, whose transmission fluid is being monitored, may provide the 12-volt power supply. The vehicle's 12-volt power supply is represented by block 10 ("12 V SUPPLY"). Referring to FIGS. 1 through 3, a 5-volt converter (block 11, "12 V TO 5 V CONV") is connected to a 12-volt power supply to reduce the voltage that is supplied to a microprocessor 15 and a fluid characteristic sensor 14, which is further shown in FIG. 3.

In another embodiment, the automatic transmission fluid monitoring system may provide its own independent power supply. This power supply may be a 12-volt power supply or a 5-volt power supply. Referring to FIG. 1, the independent 12-volt power supply is represented by block 10a ("12 V SUPPLY A") and is connected to the 12-volt-to-5-volt converter 11. Obviously, the vehicle's 12-volt power supply 10 would not be needed by the system, if the above independent power supply is installed in the system. Alternatively, a separate 5-volt power supply may serve as an independent power supply, as shown by block 12 ("5 V SUPPLY") in FIG. 1. Furthermore, if the independent 5-volt power supply is already in the system, the converter 11 and the 12-volt power supply 10 or 10a would not be needed. The present invention is not limited to the above described embodiments, and, other ways of supplying power to the fluid characteristic sensor 14, microprocessor 15, and readout 16 or 17 are possible. Depending on the characteristics of each particular part of the invention, a different voltage supply may be needed.

Referring to FIG. 1, the 5-volt power supply is used to drive the fluid characteristic sensor 14, the microprocessor 15 and the readout 16 or 17. The readout apparatus may be in a form of a dashboard 16 ("DASHBOARD READ OUT") or a tool diagnostic readout 17 ("TOOL READ OUT"), which may produce either digital or analog output. When the transmission fluid monitoring system is used as a maintenance or repair tool, readout means 17 are used to display the output. However, when the transmission fluid monitoring system is used to provide the operator or the driver of the motor vehicle with the current information and data as to the condition and health of the automatic transmission system, the readout means 16 are used to display the output. The readout means 16 is located on a dashboard of the motor vehicle. It is displayed together with temperature of the engine, speed, oil pressure, etc. of the motor vehicle.

Referring to FIGS. 1 and 3, the fluid characteristic in-line sensor is represented by block 14. The in-line sensor is located in the conduit or line 33, carrying the ATF, represented by arrow 80. Referring to FIG. 3, the in-line sensor 45 is fitted into the conduit 33 carrying the ATF. The flow of ATF is dependent on the radius of the conduit 33 and if the radius of the conduit 33 is either increased or decreased, the flow rate and the pressure of the ATF are changed accordingly. The in-line sensor 45 may have at least three sensing element means A, B and C. Each of these may measure one of the characteristics of ATF, e.g., the fluid's pressure, the fluid's flow rate, and, optionally, the fluid's temperature.

These characteristics are subject to change from point to point in the conduit 33, during the operation of the motor vehicle. However, the characteristics' values are well known and are set by the manufacturer and/or the designer of the motor vehicle's automatic transmission system.

The in-line sensor 45 is a conventionally known apparatus and may be easily obtained on the market. Referring to FIG. 3, clamps 47 and 48 securely attach in-line sensor 45 to the conduit 33 to ensure integrity and precision of the system measurements. The clamps 47 and 48 are designed so that when the motor vehicle is in operating condition and in motion, the in-line sensor 45 is not disturbed by the vibration of the motor vehicle's engine and impacts of the motor vehicle meeting the pavement irregularities, while moving.

Referring to FIG. 2, a front-wheel drive land motor vehicle is shown having a body 20 and four wheels 21, 22, 23 and 24. The front-wheels 21 and 22 are coupled to an automatic transaxle 25, which is connected to an internal combustion engine 27. The internal combustion engine 27 is connected to a heat exchange unit 28, which is commonly known as the radiator. In one embodiment, the engine is a liquid cooled engine, because the ATF is present in the form of a fluid moving through the engine cooling and lubricating it. Yet in another embodiment, the engine may be an air cooled engine, as both types, air and liquid, cooling systems are conventionally well known and readily available on the market.

The internal combustion engine 27 has a pump (not shown) for circulating the automatic transmission liquid through the engine and into the heat exchange unit. The liquid exits and enters the heat exchange unit 28 through the two passageways 31 and 32, as shown in FIG. 2. The heat exchange unit 28 cools the liquid as it passes through the unit and continues to circulate back into the engine 27. The ATF is circulating through the heat exchange unit 28 under pressure created by the engine's pump (not shown). Through its circulation, the ATF lubricates and cools the automatic transmission system 25, thus, allowing for uninterrupted operation of the motor vehicle. The ATF's rate of circulation is set at some predetermined value by the manufacturer of the automatic transmission. The cooling system of a land motor vehicle, along with all above mentioned components, is well known. The cooling system is required to maintain the engine at an operating temperature and to prevent breakdown of the engine due to overheating.

Referring to FIG. 2, the motor vehicle 40 is presented having a front-wheel drive. The conduit 33 is attached to the heat exchange unit 28 and the internal combustion engine 27. The ATF circulates through the conduit 33 in directions 34 and 35, as shown in FIG. 2. The in-line sensor 45 is inserted into the conduit 33 and is connected with the microprocessor 50 and the readout means 52. The microprocessor 50 receives data from the characteristic fluid sensor means A, B and C (as explained above in connection with FIG. 3), which are inserted as a part of the in-line sensor 45. The readout means 52 may be digital or analog. Moreover, the readout means 52 may be located on the dashboard of the motor vehicle 40 or be a separate diagnostic tool used in repair and/or maintenance. The digital read out is preferred for the purposes of repair and/or maintenance. The data shows the health and/or status of the automatic transmission system of the motor vehicle.

Referring to FIG. 2a, a rear-wheel drive land motor vehicle is shown having an internal combustion engine 60, an automatic transmission 62, a differential drive 64, a drive shaft 63 connecting the automatic transmission to the differential drive 64. The heat exchange unit 28a may be a radiator, such as heat exchange unit 28, as shown in FIG. 2. The ATF circulates in conduits 33a and 36. These conduits are longer than the corresponding conduits in the front-wheel drive vehicle, shown in FIG. 2, because of the location of the automatic transmission 62. The in-line fluid sensor 45, having identical structure to the one shown in FIG. 3, is placed into the conduit 33a. The in-line sensing element means A, B and C serve as characteristic sensor means for measuring ATF's flow rate, pressure and, optionally, the ATF's temperature. As in the front-wheel motor vehicle, a microprocessor 50a and a readout means 52a are connected to the in-line fluid sensor 45. In one embodiment, the microprocessor 50a and the readout means 52a may be combined into a single block, as shown in FIG. 2a. Again, the readout means 52a may be located on the dashboard of the motor vehicle or be a separate diagnostic tool used in maintenance and/or repair. The operation of the ATF in the rear-wheel dive motor vehicle does not differ from the operation of the ATF in the front-wheel drive motor vehicle.

In the foregoing description of the invention, referenced to the drawings, certain terms have been used for conciseness, clarity and comprehension. However, no unnecessary limitations are to be implied from or because of the terms used, beyond the requirements of the prior art, because such terms are used for descriptive purposes and are intended to be broadly construed. Furthermore, the description and illustration of the invention are used by way of example and the scope of the invention is not limited to the exact details shown, represented or described.

Having now described a preferred embodiment of the invention, in terms of features, discoveries and principles, along with certain alternative construction and suggested changes, other changes that may become apparent to those skilled in the art may be made, without departing from the scope of the invention defined in the appended claims.

What is claimed is:

1. An apparatus for monitoring the characteristics of an automatic transmission liquid means circulating in an automatic transmission system of a motor vehicle during operation of said motor vehicle, said automatic transmission system comprising a conduit means for conducting an automatic transmission liquid means from an automatic transmission to and from a heat exchange means and to said automatic transmission;

said conduit means having a monitoring means further comprising:
        a sensor means in said conduit means and positioned in a flow path of an automatic transmission liquid means in said conduit means;
        said sensor means, comprising
            a sensor element means responsive to characteristics of an automatic transmission liquid means for providing data corresponding said characteristics of an automatic transmission liquid means; and
    a microprocessor means coupled to said sensor means for receiving said data corresponding to said characteristics of an automatic transmission liquid means and converting said data into values corresponding to said characteristics of an automatic transmission liquid means.

2. The apparatus in claim 1, further comprising a readout means coupled to said microprocessor means for receiving said values corresponding to said characteristics of an automatic transmission liquid means and displaying said values corresponding to said characteristics of an automatic transmission liquid means.

3. The apparatus in claim 1, wherein said sensor means may have at least three said sensor element means.

4. The apparatus in claim 1, wherein said characteristics of an automatic transmission liquid means are rate of flow, pressure and temperature of an automatic transmission liquid means.

5. The apparatus in claim 4, wherein said rate of flow, said pressure and said temperature are converted by said microprocessor and displayed by said readout means.

6. The apparatus in claim 1, wherein said readout means is a display in a motor vehicle.

7. The apparatus in claim 6, wherein said display is in digital form.

8. The apparatus in claim 6, wherein said display is in analog form.

9. The apparatus in claim 1, wherein said readout means is a display remote from said motor vehicle.

10. The apparatus in claim 9, wherein said display is in digital form.

11. The apparatus in claim 9, wherein said display is in analog form.

12. The apparatus in claim 1, wherein said apparatus is used to detect and display said temperature, said rate of flow and said fluid pressure while said motor vehicle is in operating condition or in motion.

13. The apparatus in claim 1, wherein said apparatus is used to detect and display said temperature, said rate of flow and said fluid pressure for repair and/or maintenance purposes.

* * * * *